(12) United States Patent
May et al.

(10) Patent No.: US 6,723,395 B2
(45) Date of Patent: Apr. 20, 2004

(54) CHIRAL COMPOUNDS

(75) Inventors: Alison Linda May, Dorset (GB); Simon Greenfield, Dorset (GB); Mark John Goulding, Hampshire (GB); Owain Llyr Parri, Dorset (GB)

(73) Assignee: Merck Patent GmbH, Darmstadt (DE)

( * ) Notice: Subject to any disclaimer, the term of this patent is extended or adjusted under 35 U.S.C. 154(b) by 93 days.

(21) Appl. No.: 10/184,891

(22) Filed: Jul. 1, 2002

(65) Prior Publication Data
US 2003/0026922 A1 Feb. 6, 2003

(30) Foreign Application Priority Data
Jul. 2, 2001 (EP) .............................. 01114896

(51) Int. Cl.$^7$ ................. C09K 19/36; C09K 19/58; C09K 19/34; C09K 19/32; C07D 307/93
(52) U.S. Cl. ............. 428/1.1; 252/299.61; 252/499.62; 252/299.2; 252/299.7; 349/106; 349/185; 549/435
(58) Field of Search ...................... 428/1.1; 252/299.61, 252/299.62, 299.2, 299.7; 349/106, 185; 549/435

(56) References Cited

U.S. PATENT DOCUMENTS

| | | | | |
|---|---|---|---|---|
| 5,780,629 A | * | 7/1998 | Etzbach et al. | 544/296 |
| 5,827,449 A | * | 10/1998 | Hanelt et al. | 252/299.62 |
| 6,099,758 A | * | 8/2000 | Verrall et al. | 252/585 |
| 6,217,792 B1 | * | 4/2001 | Parri et al. | 252/299.61 |
| 6,417,902 B1 | * | 7/2002 | Greenfield et al. | 349/115 |

FOREIGN PATENT DOCUMENTS

GB 2330139 * 4/1999

* cited by examiner

Primary Examiner—Shean C. Wu
(74) Attorney, Agent, or Firm—Millen, White, Zelano & Branigan, P.C.

(57) ABSTRACT

The invention relates to chiral compounds of formula I,

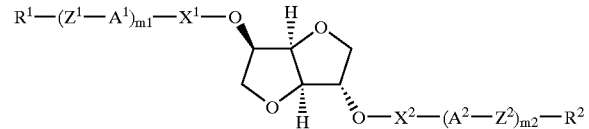

to liquid crystal mixtures comprising at least one chiral compound of formula I, to chiral linear or crosslinked liquid crystal polymers obtainable by polymerizing a polymerizable mixture comprising at least one chiral compound of formula I, to the use of chiral compound of formula I and mixtures and polymers obtained thereof in liquid crystal displays, active and passive optical elements, adhesives, synthetic resins with anisotropic mechanical properties, cosmetic and pharmaceutical compositions, diagnostics, liquid crystal pigments, for decorative and security applications, nonlinear optics, optical information storage or as chiral dopants, and to a liquid crystal display comprising a mixture comprising at least one chiral compound of formula I.

20 Claims, No Drawings

CHIRAL COMPOUNDS

FIELD OF THE INVENTION

The invention relates to chiral compounds with a high helical twisting power, to liquid crystal mixtures comprising them, and to chiral linear or crosslinked liquid crystal polymers obtained from a polymerizable mixture comprising one or more chiral compounds. The invention further relates to the use of the chiral compounds and the mixtures and polymers obtained thereof in liquid crystal displays, active and passive optical elements, adhesives, synthetic resins with anisotropic mechanical properties, cosmetic and pharmaceutical compositions, diagnostics, liquid crystal pigments, for decorative and security applications, nonlinear optics, optical information storage or as chiral dopants.

BACKGROUND AND PRIOR ART

For many applications it is desirable to have LC (Liquid Crystal) mixtures with a twisted phase. Among these are e.g. phase-change displays, guest-host displays, passive and active matrix TN and STN displays like AMD-TN, ferroelectric displays and cholesteric displays like SSCT (surface stabilized cholesteric texture) or PSCT (polymer stabilized cholesteric texture) displays, including displays with temperature compensated characteristics, e.g. by appropriate selection of the cholesteric compounds according to the invention either alone or in combination with further chiral dopants. For these applications it is advantageous to have available a chiral dopant with a high HTP (Helical Twisting Power) in order to reduce the amount of dopant needed to induce the desired pitch.

For some applications it is desired to have LC mixtures that exhibit a strong helical twist and thereby a short pitch length. For example in liquid crystal mixtures that are used in selectively reflecting cholesteric displays like SSCT or PSCT, the pitch has to be selected such that the maximum of the wavelength reflected by the cholesteric helix is in the range of visible light. Another possible application is in polymer films with a chiral liquid crystal phase for optical elements, such as cholesteric broadband polarizers or retardation films.

In a cholesteric LC material, the pitch p of the molecular helix in the first approximation, which is sufficient for most practical applications, is inversely proportional to the concentration c of the chiral dopant in the liquid crystal host mixture according to equation (1):

$$p = \frac{1}{HTP} \cdot \frac{1}{c} \quad (1)$$

The proportionality factor is the helical twisting power (HTP) of the chiral dopant.

As can be seen from equation (1), a short pitch can be achieved by using high amounts of dopant or by using a dopant with a high HTP. However, the chiral dopants of prior art often exhibit low values of the HTP, so that high amounts of dopant are needed. This is a disadvantage because chiral dopants can be used only as pure enantiomers and are therefore expensive and difficult to synthesize.

Furthermore, when using chiral dopants of prior art in high amounts, they often negatively affect the properties of the liquid crystal host mixture, e.g., the clearing point, the dielectric anisotropy Δε, the viscosity, the driving voltage or the switching times.

The chiral dopants often show a high temperature dependence of the helical twisting power. When used in cholesteric mixtures this leads to a strong temperature dependence of the reflection wavelength of the mixture. This is especially disadvantageous for application in cholesteric displays, such as SSCT displays, where usually a low temperature dependence of the reflection wavelength is required.

Another disadvantage of prior art chiral compounds is that they often show low solubility in the liquid crystal host mixture, which leads to undesired crystallization at low temperatures. To overcome this disadvantage, typically two or more different chiral dopants have to be added to the host mixture. This implies higher costs and also requires additional effort for temperature compensation of the mixture because different dopants have to be selected such that their temperature coefficients of the twist compensate each other.

There is thus a considerable demand for chiral compounds with a high HTP which are easy to synthesize, can be used in low amounts, show low temperature dependence of the twisting power, e.g., for utilizing a constant reflection wavelength, do not affect the properties of the liquid crystal host mixture and show good solubility in the host mixture.

SUMMARY OF THE INVENTION

One of the first aims of the invention is providing chiral compounds having these properties, but which do not have the disadvantages of the chiral dopants of the state of the art as discussed above. Another aim of the invention is to extend the pool of chiral dopants available to the expert.

These aims and others can be achieved by providing chiral isosorbide derivatives as described below.

WO 95/16007 and WO 98/00428 disclose chiral mesogenic compounds with a high HTP based on 1,4:3,6-Dianhydro-D-sorbitol (isosorbide). However, many of these compounds do only have a limited solubility in liquid crystal host mixtures.

Chiral compounds derived from isosorbide

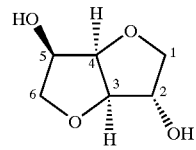

which are substituted unsymmetrically with two different mesogenic groups in the 2- and 5-position show a higher solubility in liquid crystal host mixtures compared to isosorbide derivatives that are substituted symmetrically with two identical mesogenic groups. Furthermore, the unsymmetrically substituted isosorbides show a remarkable difference in solubility depending on the respective position of the mesogenic groups. An isosorbide derivative with a larger mesogenic group, like a two-ring group, attached in 5-position and a smaller mesogenic group, like a one-ring group, attached in 2-position, for example, has a considerably higher solubility than its corresponding isomer where the two-ring group is attached in 2-position and the one-ring group in 5-position. This is a considerable unexpected improvement over the prior art.

One object of the present invention is chiral compounds of formula I

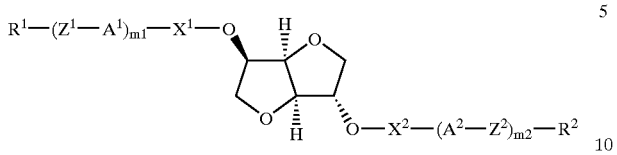

wherein
$R^1$ and $R^2$ are, independently of each other, P—Sp—X, F, Cl, Br, I, CN, SCN, $SF_5$, or a straight chain or branched alkyl with up to 30 C atoms that is unsubstituted, mono- or poly-substituted by F, Cl, Br, I or CN, and wherein one or more non-adjacent $CH_2$ groups are optionally replaced, in each case independently from one another, by —O—, —S—, —NH—, —$NR^0$—, —CO—, —COO—, —OCO—, —OCO—O—, —S—CO—, —CO—S—, —CH=CH— or —C≡C— in a manner that O and/or S atoms are not linked directly to one another,
$R^0$ is H or alkyl with 1 to 4 C atoms,
P is a polymerizable group,
Sp is a spacer group or a single bond,
X is —O—, —S—, —$OCH_2$—, —$CH_2O$—, —CO—, —COO—, —OCO—, —OCO—O—, —CO—$NR^0$—, —$NR^0$—CO—, —$OCH_2$—, —$CH_2O$—, —$SCH_2$—, —$CH_2S$—, —CH=CH—COO—, —OOC—CH=CH— or a single bond,
$X^1$ is —CO—, —OCO—, —$NR^0$—CO—, —CH=CH—CO—, —$CH_2$—, —$C_2H_4$—, —$CF_2$— or a single bond,
$X^2$ is —CO—, —COO—, —CO—$NR^0$—, —CO—CH=CH—, —$CH_2$—, —$C_2H_4$—, —$CF_2$— or a single bond,
$Z^1$ and $Z^2$ are independently of each other —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=CH—, —CF=CH—, —CH=CF—, —CF=CF—, —C≡C—, —CH=CH—COO—, —OCO—CH=CH— or a single bond,
$A^1$ and $A^2$ are, independently of each other, an aliphatic or aromatic carbocyclic or heterocyclic group with up to 16 C atoms that optionally contains one or more fused rings and is unsubstituted, mono- or polysubstituted with L,
L is halogen or a cyano, nitro, alkyl, alkoxy, alkylcarbonyl or alkoxycarbonyl group with 1 to 7 C atoms, wherein one or more H atoms are optionally substituted by F or Cl,
$m^1$ is 1, 2 or 3, and
$m^2$ is 0, 1, 2 or 3,
with the proviso that the total number of fused or unfused rings in the $(Z^1-A^1)_{m1}$ group is larger than in the $(A^2-Z^2)_{m2}$ group.

Another object of the invention is a liquid crystal mixture containing at least one compound of formula I.

Another object of the present invention is a polymerizable liquid crystal mixture comprising at least one compound of formula I.

Another object of the invention is a linear or crosslinked anisotropic polymer with twisted structure obtainable from a polymerizable liquid crystal mixture comprising one or more compounds of formula I.

A further object of the invention is the use of compounds of formula I or a liquid crystal mixture or anisotropic polymer film comprising them in liquid crystal displays, such as STN, TN, AMD-TN, temperature compensation, ferroelectric, guest-host, phase change or surface stabilized or polymer stabilized cholesteric texture (SSCT, PSCT) displays, in active and passive optical elements like polarizers, compensators, alignment layers, color filters or holographic elements, in adhesives, synthetic resins with anisotropic mechanical properties, cosmetic and pharmaceutical compositions, diagnostics, liquid crystal pigments, for decorative and security applications, in nonlinear optics, optical information storage or as chiral dopants.

Yet another object of the invention is a liquid crystal display comprising a liquid crystal mixture comprising at least one chiral compound of formula I.

DETAILED DESCRIPTION OF THE INVENTION

The inventive chiral compounds bear numerous advantages, for example,
they exhibit a high HTP,
they exhibit a good solubility in liquid crystal mixtures,
when inventive compounds are used as chiral dopant in a liquid crystal mixture, due to their high solubility, higher amounts of dopant can be used to produce a high twist (=a low pitch),
due to their high HTP, lower amounts of inventive dopants are needed to achieve a high pitch, and thereby the liquid crystalline properties of the mixture are less negatively affected,
enantiomerically pure inventive chiral compounds are easy to prepare.

The inventive chiral compounds are mesogenic or even liquid crystalline, i.e., they can induce or enhance mesophase behavior, for example, in admixture with other compounds, or even exhibit one or more mesophases themselves. It is also possible that the inventive compounds show mesophase behavior only in mixtures with other compounds, or, in case of polymerizable compounds, when being (co)polymerized. Mesogenic inventive chiral compounds are especially preferred.

In formula I, $Z^1$ adjacent to $R^1$ and $Z^2$ adjacent to $R^2$ are preferably a single bond.

Preferred groups $A^1$ and $A^2$ in formula I are, for example, cyclopentane, 1,1,-dimethylcyclopentane, tetrahydrofuran, pyrrolidine, furan, pyrrol, thiophene, oxazole, thiazole, thiadiazole, imidazole, pyrrolidinone, cyclohexane, cyclohexene, tetrahydropyran, piperidine, tetrahydrothiopyrane, dioxane, dithiane, oxathiane, thiomorpholine, morpholine, phenylene, pyridine, pyrimidine, pyrazine, bicyclohexane, bicyclohexene, cyclohexane-1,4-dione, bicyclo[2,2,2]octylene, cyclohexenone, indane, naphthalene, decahydronaphthalene, 1,2,3,4-tetrahydronaphthalene, anthracene and phenanthrene.

Particularly preferably $A^1$ and $A^2$ are 1,4-phenylene in which one or more CH groups may be replaced by N, 1,4-cyclohexylene in which one or two non-adjacent $CH_2$ groups may be replaced by O and/or S, 1,3-dioxolane-4,5-diyl, 1,4-cyclohexenylene, 1,4-bicyclo-(2,2,2)-octylene, piperidine-1,4-diyl, naphthalene-2,6-diyl, decahydronaphthalene-2,6-diyl, 1,2,3,4-tetrahydronaphthalene-2,6-diyl and indane-2,5-diyl, it being possible for all these groups to be unsubstituted, mono- or polysubstituted by L as defined above.

Especially preferred are compounds of formula I wherein the groups $(Z^1-A^1)_{m1}$ and $(A^2-Z^2)_{m2}$ contain only monocyclic groups $A^1$ and $A^2$, with m1>m2.

Of these preferred compounds, especially preferred are those wherein $A^1$ and $A^2$ are selected from aliphatic and aromatic six-membered carbocycles that may also contain one or more hetero atoms, very preferably from 1,4-phenylene in which, in addition, one or more CH groups may be replaced by N, 1,4-cyclohexylene in which, in addition, one or two non-adjacent $CH_2$ groups may be replaced by O and/or S, 1,3-dioxolane-4,5-diyl, 1,4-cyclohexenylene and piperidine-1,4-diyl, it being possible for all these groups to be unsubstituted, mono- or polysubstituted with L as defined in formula I.

A group of preferred groups $(Z^1-A^1)_{m1}$ and $(A^2-Z^2)_{m2}$ is listed below. For reasons of simplicity, Phe in these groups is 1,4-phenylene which may be also substituted by one or more L groups as defined in formula I, and Cyc is 1,4-cyclohexylene. The following list of groups is preferred as well as their mirror images

| | |
|---|---|
| -Phe- | II-1 |
| -Cyc- | II-2 |
| -Phe-Z-Phe- | II-3 |
| -Phe-Z-Cyc- | II-4 |
| -Cyc-Z-Cyc- | II-5 |
| -Phe-Z-Phe-Z-Phe- | II-6 |
| -Phe-Z-Phe-Z-Cyc- | II-7 |
| -Phe-Z-Cyc-Z-Phe- | II-8 |
| -Cyc-Z-Phe-Z-Cyc- | II-9 |
| -Cyc-Z-Cyc-Z-Phe- | II-10 |
| -Cyc-Z-Cyc-Z-Cyc- | II-11 |

Especially preferred are formulae II-1, II-2, II-3, II-4 and II-5. Further preferred are groups $(Z^1-A^1)_{m1}$ and $(A^2-Z^2)_{m2}$ comprise at least one Phe group that is substituted with one or two L groups, preferably in the 2- and/or 3-position, and L is F, Cl, $CH_3$, $OCH_3$, $CF_3$, $CHF_2$, $CH_2F$, $OCF_3$ $OCHF_2$, $OCH_2F$ or CN.

Further preferred are compounds of formula I, wherein m1 is 1 and m2 is 0 or 1.

m1 is 2 and m2 is 1.

$X^1$ and $X^2$ are —CO—.

$Z^1$ and $Z^2$ are independently of each other —COO—, —OCO— or a single bond.

$R^1$ and/or $R^2$ is a polymerizable P—Sp—X group.

$R^1$ and $R^2$ are straight chain or branched alkyl or alkoxy with 1 to 12 C atoms.

L is F, Cl, CN, $NO_2$, $CH_3$, $C_2H_5$, $OCH_3$, $OC_2H_5$, $COCH_3$, $COC_2H_5$, $CF_3$, $CHF_2$, $CH_2F$, $OCF_3$ $OCHF_2$, $OCH_2F$ or $OC_2F_5$.

$A^1$ and $A^2$ are, independently of each other, trans-1,4-cyclohexylene or 1,4-phenylene, the latter being unsubstituted or substituted with up to 4, preferably 1 or 2 L groups, preferably in the 3- and/or 5-position or in the 2- and/or 3-position, with L being preferably F, $C_1$, $CH_3$, $OCH_3$, $CF_3$, $CHF_2$, $CH_2F$, $OCF_3$ $OCHF_2$, $OCH_2F$ or CN.

$A^1$ and $A^2$ are unsubstituted 1,4-phenylene.

L is preferably F, Cl, CN, $NO_2$, $CH_3$, $C_2H_5$, $OCH_3$, $OC_2H_5$, $COCH_3$, $COC_2H_5$, $CF_3$, $CHF_2$, $CH_2F$, $OCF_3$ $OCHF_2$, $OCH_2F$, $OC_2F_5$, in particular F, Cl, CN, $CH_3$, $CHF_2$, $C_2H_5$, $OCH_3$, $OCHF_2$, $CF_3$ or $OCF_3$, most preferably F, $CH_3$, $CF_3$, $OCH_3$, $OCHF_2$ or $OCF_3$.

If $R^1$ or $R^2$ in formula I is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e., where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

Halogen is preferably F or Cl.

$R^1$ or $R^2$ in formula I can be a polar or a non-polar group. In case of a polar group, it is CN, $SF_5$, halogen, $OCH_3$, SCN, $COR^5$, $COOR^5$, or a mono-, oligo- or polyfluorinated alkyl or alkoxy group with 1 to 4 C atoms. $R^5$ is optionally fluorinated alkyl with 1 to 4, preferably 1 to 3 C atoms. Especially preferred polar groups are F, Cl, CN, $OCH_3$, $COCH_3$, $COC_2H_5$, $COOCH_3$, $COOC_2H_5$, $CF_3$, $CHF_2$, $CH_2F$, $OCF_3$, $OCHF_2$, $OCH_2F$, $C_2F_5$ and $OC_2F_5$, in particular F, Cl, CN, $CF_3$, $OCHF_2$ and $OCF_3$. In case of a non-polar group, it is preferably alkyl with up to 15 C atoms or alkoxy with 2 to 15 C atoms.

$R^1$ or $R^2$ in formula I can be an achiral or a chiral group. In case of a chiral group it is preferably of formula III:

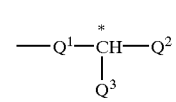

III wherein $Q^1$ is an alkylene or alkylene-oxy group with 1 to 9 C atoms or a single bond, $Q^2$ is an alkyl or alkoxy group with 1 to 10 C atoms which may be unsubstituted, mono- or polysubstituted by F, Cl, Br or CN, it being also possible for one or more non-adjacent $CH_2$ groups to be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another, $Q^3$ is F, Cl, Br, CN or an alkyl or alkoxy group as defined for $Q^2$, but being different from $Q^2$.

In case $Q^1$ in formula III is an alkylene-oxy group, the O atom is preferably adjacent to the chiral C atom.

Preferred chiral groups of formula III are 2-alkyl, 2-alkoxy, 2-methylalkyl, 2-methylalkoxy, 2-fluoroalkyl, 2-fluoroalkoxy, 2-(2-ethin)-alkyl, 2-(2-ethin)-alkoxy, 1,1,1-trifluoro-2-alkyl and 1,1,1-trifluoro-2-alkoxy.

Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Compounds of formula I containing an achiral branched group $R^1$ or $R^2$ are of importance, for example, due to their reduction in the tendency towards crystallization. Branched groups of this type generally do not contain more than one branch. Preferred achiral branched groups are isopropyl, isobutyl (=methylpropyl), isopentyl (=3-methylbutyl), isopropoxy, 2-methyl-propoxy and 3-methylbutoxy.

The polymerisable group P is preferably
$CH_2=CW^1—COO—$

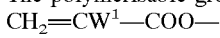, 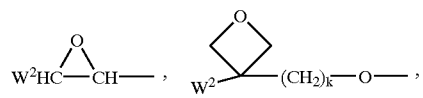, $CH_2=CW^2—(O)_{k1}—$, $CH_3—CH=CH—O—$, $HO—CW^2W^3—$, $HS—CW^2W^3—$, $HW^2N—$, $HO—CW^2W^3—NH—$, $CH_2=CW^1—CO—NH—$, $CH_2=CH—(COO)_{k1}$-Phe-$(O)_{k2}—$, Phe-$CH=CH—$, $HOOC—$, $OCN—$ and $W^4W^5W^6Si—$, wherein $W^1$ is H, Cl, CN, phenyl or alkyl with 1 to 5 C-atoms, in particular H, $C_1$ or $CH_3$, $W^2$ and $W^3$ are, independently of each other, H or alkyl with 1 to 5 C-atoms, in particular methyl, ethyl or n-propyl, $W^4$, $W^5$ and $W^6$ are, independently of each other, Cl, oxaalkyl or oxacarbonylalkyl with 1 to 5 C-atoms, Phe is 1,4-phenylene, and $k_1$ and $k_2$ are, independently of each other, 0 or 1.

More preferably P is a vinyl group, an acrylate group, a methacrylate group, a propenyl ether group or an epoxy group, especially preferably, an acrylate or a methacrylate group.

Spacer group Sp can be any group that is known for this purpose to the skilled in the art. Spacer group Sp is preferably a linear or branched alkylene group having 1 to 20 C atoms, in particular 1 to 12 C atoms, in which one or more non-adjacent $CH_2$ groups may be replaced by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, wherein $R^0$ and $R^{00}$ are, independently of each other, H or alkyl with 1 to 4 C-atoms.

Typical spacer groups are, for example, —$(CH_2)_p$—, —$(SiR^0R^{00}—O)_p$—, —$(CH_2CH_2O)_r$—$CH_2CH_2$—, —$CH_2CH_2$—S—$CH_2CH_2$— or —$CH_2CH_2$—NH—$CH_2CH_2$—, wherein p is an integer of 2 to 12, and r is an integer of 1 to 3.

Preferred spacer groups, for example, are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene.

Especially preferred are chiral compounds of formula I wherein Sp-X is alkylene or alkylene-oxy with 2 to 6 C atoms. Straight-chain groups are especially preferred.

In another preferred embodiment of the invention the chiral compounds contain at least one spacer group Sp that is a chiral group of formula IV:

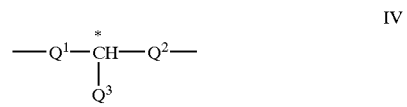

IV wherein
$Q^1$ is an alkylene or alkylene-oxy group with 1 to 10 C atoms or a single bond,
$Q^2$ is an alkylene or alkylene-oxy group with 1 to 10 C atoms or a single bond, which is different from $Q^1$, and
$Q^3$ is halogen, a cyano group or an alkyl or alkoxy group with 1 to 4 C atoms, which is different from $Q^2$.

In case $Q^1$ in formula IV is an alkylene-oxy group, the O atom is preferably adjacent to the chiral C atom.

Particularly preferred compounds of formula I are

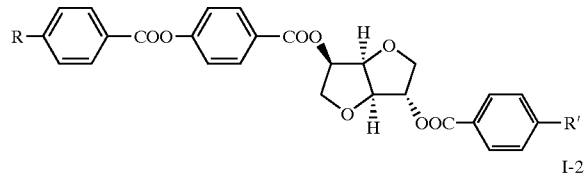

I-1

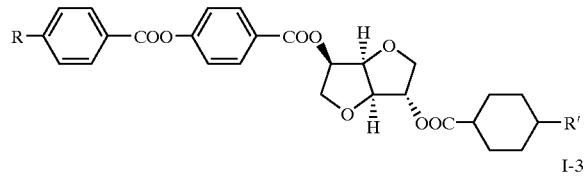

I-2

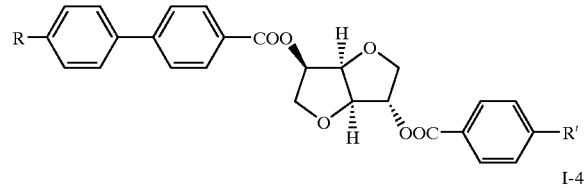

I-3

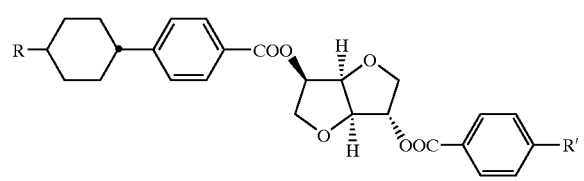

I-4

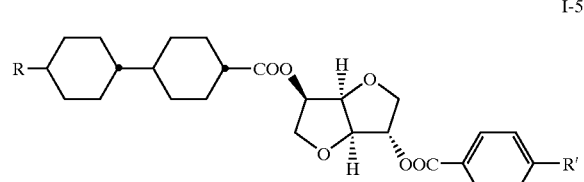

I-5

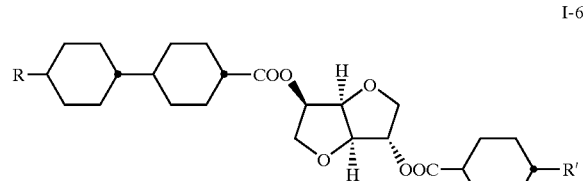

I-6 wherein R and R' have one of the meanings of $R^1$ in formula I and wherein any phenylene ring may be substituted by 1, 2 or 3 L groups.

In these preferred compounds R and R' are preferably alkyl or alkoxy with 1 to 12 C atoms or P—Sp—X— as defined above. Compounds having one or more substituted phenylene rings are preferably substituted in 2-, 3-2- and 3- or 3- and 5-position with F, Cl, $CH_3$, $OCH_3$ or CN.

The inventive chiral compounds can be synthesized according to, or in analogy to, known methods as described, for example, in WO 98/00428.

The preparation of unsymmetrical isosorbides of formula I is possible due to a difference in reactivity between the two hydroxy groups on the isosorbide. The 2-position in the isosorbide is least hindered and therefore reacts preferentially. Selective esterification of 1,4:3,6-Dianhydro-D-glucitol is described in Z. Cekovic and Z. Tokic, Communications, Synthesis, p. 610–612 (1989). It is possible to utilize this method to prepare, e.g., monoesters of isosorbide, and then to react the other hydroxy groups with a different acid.

Further methods of synthesis are illustrated in the examples.

The chiral compounds of formula I can be used in a liquid crystal mixture for displays exhibiting a helically twisted molecular structure of the liquid crystal matrix, for example, TN displays of the active or passive matrix type, STN, phase-change, guest-host, ferroelectric or cholesteric displays like SSCT (surface stabilized cholesteric texture) or PSCT (polymer stabilized cholesteric texture).

Thus, another object of the invention is a liquid crystal mixture, in particular a chiral smectic or cholesteric liquid crystal mixture, comprising at least one chiral compound of formula I.

Yet another object of the invention is a liquid crystal display comprising a liquid crystal medium containing at least one chiral compound of formula I.

The chiral compounds of formula I exhibit high values of the HTP. Preferred values of the HTP are $\geq 20$, more preferably $\geq 40$, in particular $\geq 60$ $\mu m^{-1}$. This enables the preparation of liquid crystal mixtures with a high helical twist, i.e., a low pitch, by using only low amounts of chiral compounds of formula I. This is a considerable advantage, as it is often observed that the addition of high amounts of chiral dopants to a liquid crystal mixture negatively affects its liquid crystal phase behavior and electrooptical properties, such as the dielectric anisotropy, the viscosity, or the clearing point. Thus, by using chiral compounds of formula I in a liquid crystal mixture or display, its properties are altered only to a minor extent; compared to prior art dopants, resulting, for example, in a lower threshold voltage and faster switching times of the display.

The chiral compounds of formula I are further characterized by a high solubility in a liquid crystal host mixture. Undesired spontaneous crystallization at low temperatures is reduced, and the operating temperature range of the mixture can be broadened. The use of a second dopant, which is often added to avoid crystallization, can thus be avoided.

A particularly preferred embodiment of the present invention therefore relates to a liquid crystal mixture comprising only one chiral compound, which is a compound of formula I, and to a display comprising such a mixture.

The chiral compounds of formula I also show a low temperature dependence of the HTP when added to a liquid crystal host mixture. They are thus useful as chiral dopants for liquid crystal mixtures and displays with a low temperature dependence of the pitch.

A liquid crystal mixture according to the invention comprises preferably 0.1 to 30%, in particular 1 to 25% and very particularly preferably 2 to 15% by weight of chiral compounds of formula I. It preferably comprises 1, 2 or 3 chiral compounds of formula I.

The compounds of formula I are especially suitable for use in cholesteric liquid crystal mixtures for cholesteric displays, in particular SSCT or PSCT displays. Cholesteric displays are described, for example, in WO 92/19695, WO 93/23496, U.S. Pat. No. 5,453,863 and U.S. Pat. No. 5,493,430.

It was found that, when using chiral compounds of formula I as dopants in liquid crystal mixtures for cholesteric displays, due to their high solubility and low temperature dependence of the HTP, a mixture with high helical twist and low temperature dependence can be achieved. Cholesteric mixtures with high brightness and low temperature dependence of the reflection color can thus be achieved even by using only one chiral dopant according to formula I. This is a considerable advantage over prior art, where it is often necessary to use two or more dopants to prevent crystallisation, and to use two dopants with opposite temperature dependence of the helical twist (e.g. one with positive temperature dependence and one with negative temperature dependence) to achieve good temperature compensation of the reflection wavelength.

Thus, a particularly preferred embodiment of the present invention relates to a cholesteric liquid crystal medium, in particular, for use in SSCT and PSCT displays, comprising one chiral dopant, which is a compound of formula I, preferably in an amount of 1 to 20%, in particular 2 to 15%.

The liquid crystal mixture preferably contains a chiral component which contains at least one chiral compound of formula I, and a nematic component comprising one or more nematic or nematogenic compounds.

Preferably the liquid crystal mixture contains 2 to 25, preferably 3 to 15 compounds, at least one of which is a chiral compound of formula I. The other compounds, forming the nematic component, are preferably low molecular weight liquid crystal compounds which are nematic or nematogenic substances, for example, azoxybenzenes, benzylidene-anilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclo-hexylcyclohexanecarboxylic acid, phenylcyclohexanes, cyclohexyl-biphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclo-hexylpyrimidines, phenyl- or cyclohexylpyridines, phenyl- or cyclo-hexylpyridazines, phenyl- or cyclohexyldioxanes, phenyl- or cyclo-hexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl2-cyclohexyl-phenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystal mixture of the preferred embodiment described above is preferably based on the above listed achival compounds.

In another embodiment, compounds that can be components of the above liquid crystal mixtures are of formula

R'-L'-G'-E-R"

wherein L' and E, which may be identical or different, are in each case, independently from one another, a bivalent radical of the group formed by -Phe-, -Cyc-, -Phe-Phe-, -Phe-Cyc-, -Cyc-Cyc-, -Pyr-, -Dio-, -B-Phe- or -B-Cyc- or their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and B is 2-(trans-1,4-cyclohexyl)ethyl, pyrimidine-2,5-diyl, pyridine-2,5-diyl or 1,3-dioxane-2,5-diyl.

G' is a bivalent group of —CH=CH—, —N(O)N—, —CH=CY—, —CH=N(O)—, —C≡C—, —CH$_2$—CH$_2$—, —CO—O—, —CH$_2$—O—, —CO—S—, —CH$_2$—S—, —CH=N—, —COO-Phe-COO— or a single bond, wherein Y is halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example, in Houben-Weyl, Methoden der Organischen Chemie [Methods of Organic Chemistry], Georg-Thieme-Verlag, Stuttgart), under reaction conditions which are known and suitable for said reactions. Use may also be made here of variants which are known per se, but are not mentioned here.

Polymerizable compounds of formula I or polymerizable liquid crystal mixtures comprising one or more compounds of formula I are useful for the preparation of polymerizable mixtures, which can be used, for example, in polymer stabilized liquid crystal displays, such as PSCT (polymer stabilized cholesteric texture) and anisotropic polymer gels, which can be used, for example, in scattering type displays. Anisotropic polymer gels and displays comprising them are disclosed, for example, in DE 195 04 224 and GB 2 279 659.

The chiral compounds of formula I and polymerizable liquid crystal mixtures comprising them are particularly useful for the preparation of anisotropic polymer films having helically twisted molecular structure with uniform planar orientation, i.e., wherein the helical axis is oriented perpendicular to the plane of the film.

Oriented cholesteric polymer films, for example, can be used as broad waveband reflective polarizers, for example, described in EP 0 606 940, WO 97/35219 and EP 0 982 605, as color filters, for security markings, or for the preparation of liquid crystal pigments for decorative or security uses.

For the preparation of anisotropic polymer gels or oriented polymer films, the liquid crystal mixture should comprise at least one polymerizable compound, which can be a compound of formula I or an additional polymerizable mesogenic or liquid crystalline compound.

Thus, another object of the invention is polymerizable liquid crystal mixtures comprising at least one chiral compound of formula I.

Examples of suitable polymerizable mesogenic compounds that can be used as components of the polymerizable liquid crystal mixture, are disclosed, for example, in WO 93/22397; EP 0,261,712; DE 195,04,224; WO 95/22586 and WO 97/00600. The compounds disclosed in these documents, however, are to be regarded merely as examples that shall not limit the scope of this invention.

Preferably, the polymerizable liquid crystal mixture comprises at least one polymerizable mesogenic compound having one polymerizable functional group and at least one polymerizable mesogenic compound having two or more polymerizable functional groups.

Examples of especially useful monoreactive chiral and achiral polymerizable mesogenic compounds are shown in the following list of compounds, which should, however, be taken only as illustrative and is in no way intended to restrict, but instead to explain the present invention:

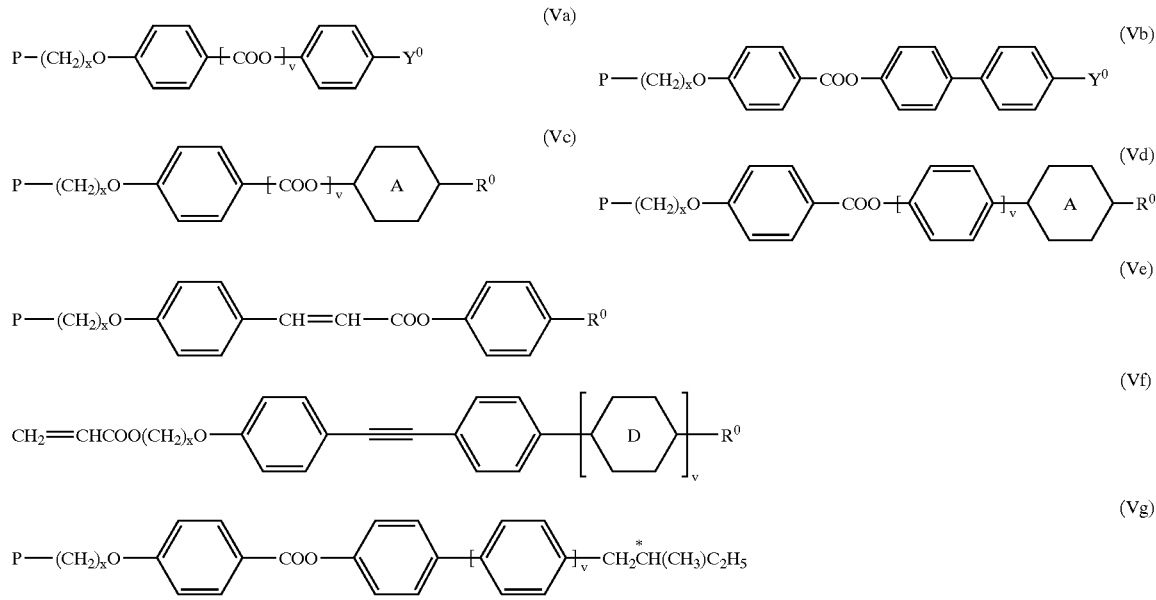

-continued

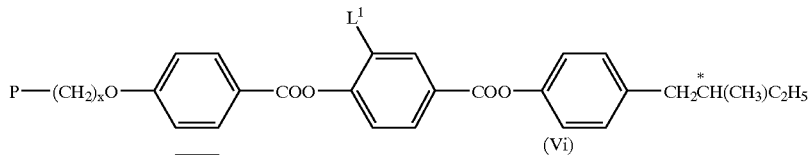
(Vh)

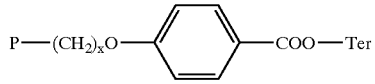
(Vi)

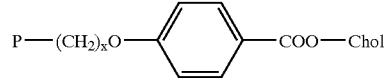
(Vk)

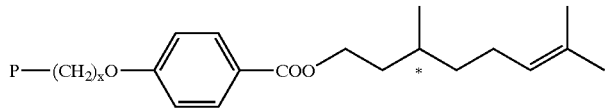
(Vm)

wherein, P has one of the meanings given above, x is an integer from 1 to 12, A and D are 1,4-phenylene or 1,4-cyclohexylene, v is 0 or 1, $Y^0$ is a polar group, $R^0$ is a non-polar alkyl or alkoxy group, Ter is a terpenoid radical, e.g., menthyl, Chol is a cholesteryl group, and $L^1$ and $L^2$ are, each independently, H, F, Cl, CN, OH, $NO_2$ or an optionally halogenated alkyl, alkoxy or carbonyl group with 1 to 7 C atoms.

The polar group $Y^0$ is preferably CN, $NO_2$, halogen, $OCH_3$, OCN, SCN, $COR^5$, $COOR^5$ or a mono- oligo- or polyfluorinated alkyl or alkoxy group with 1 to 4 C atoms. $R^5$ is optionally fluorinated alkyl with 1 to 4, preferably 1 to 3 C atoms. Especially preferably the polar group $Y^0$ is F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, or $OC_2F_5$, in particular, F, Cl, CN, $OCH_3$ or $OCF_3$.

The non-polar group $R^0$ is preferably an alkyl group with 1 or more, preferably 1 to 15 C atoms or an alkoxy group with 2 or more, preferably 2 to 15 C atoms.

Examples of useful direactive chiral and achiral polymerizable mesogenic compounds are shown in the following list of compounds, which should, however, be taken only as illustrative and is in no way intended to restrict, but instead to explain the present invention

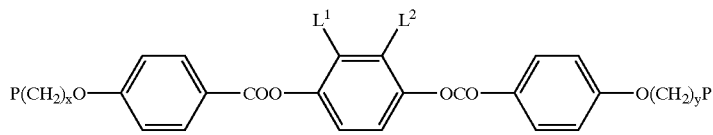
(VIa)

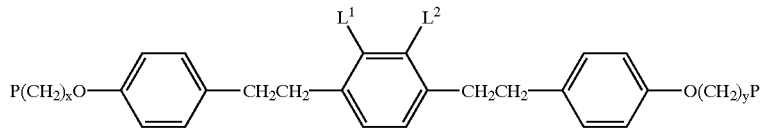
(VIb)

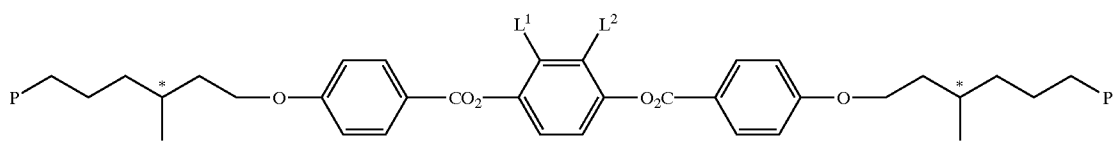
(VIc)

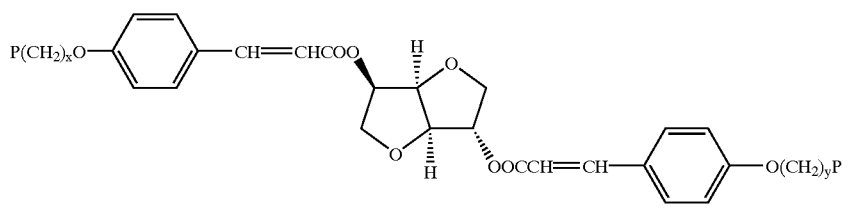
(VId)

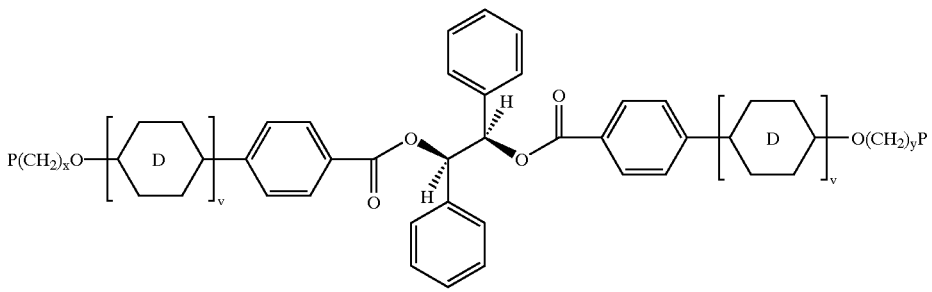

(VIe)

wherein P, x, D, $L^1$ and $L^2$ have one of the meanings given above and y is an integer of 1 to 12, the same as or different from x.

A polymerizable liquid crystal material as described above comprises one or more chiral dopants which themselves do not necessarily have to show a liquid crystal phase and give good planar alignment themselves, in particular non-polymerizable chiral dopants.

The mono- and difunctional polymerizable mesogenic compounds of above formulae V and VI can be prepared by methods which are known per se and which are described in the documents cited above and, for example, in standard works of organic chemistry, for example, Houben-Weyl, Methoden der organischen Chemie, Thieme-Verlag, Stuttgart.

In a preferred embodiment of the invention the polymerizable liquid crystal mixtures comprise at least one inventive chiral compound, at least one monofunctional compound of formulae Va–Vm and at least one bifunctional polymerizable compound of formulae VIa–VIe.

In another preferred embodiment the polymerizable liquid crystal mixtures comprise at least one inventive chiral compound and at least two monofunctional compounds of formulae Va–Vm.

Another object of the invention is an anisotropic polymer film with an oriented chiral liquid crystalline phase obtainable by (co)polymerizing a liquid crystal mixture comprising at least one chiral compound of formula I and at least one polymerizable mesogenic compound preferably of formula Va–Vm, and VIa–VIe, and/or at least one polymerizable chiral compound of formula I.

To prepare an anisotropic polymer film having a chiral liquid crystalline phase with uniform orientation, the polymerizable liquid crystal can be coated onto a substrate, aligned, and polymerized in situ, for example, by exposure to heat or actinic radiation, to fix the uniform orientation of the liquid crystal molecules. Alignment and curing are carried out in the liquid crystalline phase of the mixture.

Actinic radiation means irradiation with light, e.g., UV light, IR light or visible light, irradiation with X-rays or gamma rays, or irradiation with high energy particles, such as ions or electrons. As a source for actinic radiation, for example, a single UV lamp or a set of UV lamps can be used. Another possible source for actinic radiation is a laser, e.g., a UV laser, an IR laser or a visible laser.

For example, when polymerizing by means of UV light, a photoinitiator can be used that decomposes under UV irradiation to produce free radicals or ions that start the polymerization reaction.

It is also possible to use a cationic photoinitiator, when curing reactive mesogens with, for example, vinyl and/or epoxide reactive groups, that photocures with cations instead of free radicals.

As a photoinitiator for radical polymerization, for example, the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used.

Preferably the polymerizable liquid crystal mixture comprising polymerizable chiral compounds of formula I and/or polymerizable mesogenic compounds of formulae V and/or VI additionally comprises 0.01 to 10%, in particular 0.05 to 8%, very preferably 0.1 to 5% by weight of a photoinitiator, especially preferably a UV-photoinitiator.

Polymerization is preferably carried out under an atmosphere of inert gas, preferably under a nitrogen atmosphere.

As a substrate, for example, a glass or quartz sheet, as well as a plastic film or sheet can be used. It is also possible to put a second substrate on top of the coated mixture prior to, during and/or after polymerization. The substrates can optionally be removed after polymerization. When using two substrates in case of curing by actinic radiation, at least one substrate has to be transmissive for the polymerization.

Isotropic or birefringent substrates can be used. In case the substrate is not removed from the polymerized film after polymerization, preferably isotropic substrates are used.

Preferably at least one substrate is a plastic substrate, for example, a film of polyester such as polyethyleneterephthalate (PET), of polyvinylalcohol (PVA), polycarbonate (PC) or triacetylcellulose (TAC), especially preferably a PET film or a TAC film. As a birefringent substrate, for example, an uniaxially stretched plastic film can be used. For example PET films are commercially available from ICI Corp. under the trade name Melinex.

Preferably the polymerizable liquid crystal mixture I is coated as a thin layer on a substrate or between substrates, and aligned in its chiral mesophase into planar orientation, wherein the axis of the molecular helix extends transversely to the layer.

Planar orientation can be achieved, for example, by shearing the mixture, e.g., by means of a doctor blade. It is also possible to put a second substrate on top of the coated material. In this case, the shearing caused by putting together the two substrates is sufficient to give good alignment. Alternatively it is possible to apply an alignment layer, for example a layer of rubbed polyimide or sputtered $SiO_x$, wherein x is 1 to 2, on top of at least one of the substrates, or to apply an electric or magnetic field to the coated mixture, in order to induce or enhance planar alignment. In a preferred method, planar alignment is induced or enhanced by addition of one or more surface-active compounds to the polymerizable mixture.

In some cases it is of advantage to apply a second substrate not only to aid alignment of the polymerizable mixture, but also to exclude oxygen that may inhibit the polymerization. Alternatively, the curing can be carried out under an atmosphere of inert gas. Curing in air, however, is also possible by using one or more suitable photoinitiators and high lamp power. When using a cationic photoinitiator, oxygen exclusion most often is not necessary, but water should be excluded.

A detailed description of the in situ polymerization of polymerizable mesogenic compounds can be found, for example, in D. J. Broer et al., Makromolekulare Chemie 190, 2255 (1989).

A polymerizable liquid crystal mixture for the preparation of anisotropic polymer films comprises preferably 0.1 to 35%, in particular 0.5 to 15% and very particularly preferably 0.5 to 5% by weight of one or more polymerizable chiral compounds of formula I.

Polymerizable liquid crystal mixtures are preferred that comprise 1 to 3 chiral compounds of formula I.

The inventive polymerizable liquid crystal mixtures can additionally comprise one or more other suitable components, for example, catalysts, sensitizers, stabilizers, co-reacting monomers or surface-active compounds.

In a preferred embodiment of the invention, the inventive polymerizable liquid crystal mixture comprises a stabilizer that is used to prevent undesired spontaneous polymerization, for example, during storage of the composition. As stabilizers, in principal, all compounds can be used that are known to the skilled in the art for this purpose. These compounds are commercially available in a broad variety. Typical examples for stabilizers are 4-ethoxyphenol or butylated hydroxytoluene (BHT).

It is also possible, in order to increase crosslinking of the polymers, to add up to 20% of a non mesogenic compound with two or more polymerizable functional groups to the polymerizable composition alternatively or additionally to the multifunctional polymerizable mesogenic compounds.

Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Polymerization of inventive compositions comprising compounds with only one polymerizable functional group leads to linear polymers, whereas in the presence of compounds with more than one polymerizable functional group crosslinked polymers are obtained.

For the preparation of anisotropic polymer gels, the liquid crystal mixtures can be polymerized in situ as described above, however, in this case alignment of the polymerizable mixture is not necessary.

The inventive chiral compounds of formula I and liquid crystal mixtures, liquid crystal polymers or liquid crystal pigments comprising them are also suitable for use in cosmetic and pharmaceutical compositions, for example, in colored make-up as described in EP 815 826 or as UV-filters for the protection of human skin or hair, in particular, protection against UV-A and UV-B-radiation, as described, for example, in DE 196 29 761 or EP 1 038 941. The inventive dopants have a high HTP, therefore only small amounts are needed to yield a short pitch, resulting in a material that shows reflection in the UV range and is thus suitable as a UV-filter.

A liquid crystal mixture, liquid crystal polymer or liquid crystal pigment comprising a chiral compound of formula I which reflects UV light, in particular of a wavelength of 200 to 400 nm, is another object of the invention. Another object is a cosmetic composition, in particular, a cosmetic or pharmaceutical composition for protection of human skin or hair, comprising as UV-filter a liquid crystal mixture, a liquid crystal polymer or a liquid crystal pigment comprising a chiral compound of formula I which reflects UV light, in particular in a wavelength range of 200–440 nm, especially 280–400 nm, 200–230 nm (UV-C) and 280–330 nm (UV-B).

The values of the helical twisting power HTP of a chiral compound in a liquid crystal host are given according to the equation HTP=$(p \cdot c)^{-1}$ in $\mu m^{-1}$, wherein p is the pitch of the molecular helix, given in $\mu m$, and c is the concentration by weight of the chiral compound in the host given in relative values (thus, e.g., a concentration of 1% by weight corresponds to a value of c of 0.01.)

The following abbreviations are used to illustrate the liquid crystalline phase behavior of the compounds: C=crystalline; N=nematic; S=smectic; N*, Ch=chiral nematic or cholesteric; I=isotropic. The numbers between these symbols indicate the phase transition temperatures in degree Celsius. Furthermore, mp. is the melting point, $\Delta n$ is the birefringence at 589 nm and 20° C., and $\Delta \epsilon$ is the dielectric anisotropy at 20° C. C* in a chemical formula denotes a chiral C atom. DCC is N,N'-Dicyclohexylcarbodiimide, DMAP is 4-Dimethylaminopyridine, DCM is dichloromethane. "Conventional workup" means: water is added if necessary, the mixture is extracted with methylene chloride, diethyl ether or toluene, the phases are separated, the organic phase is dried and concentrated by evaporation, and the product is purified by crystallization and/or chromatography.

Unless indicated otherwise, the HTP values of the examples were determined in the commercially available liquid crystal host mixture BL087 (Merck KGaA, Darmstadt, Germany) at a concentration of 5% and a temperature of 20° C.

From the foregoing description, one skilled in the art can easily ascertain the essential characteristics of this invention, and without departing from the spirit and scope thereof, can make various changes and modifications of the invention to adapt it to various uses and conditions.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure[s] of all applications, patents and publications, cited above or below, and of corresponding European application No. 01114896.2, filed Jul. 2, 2001, is hereby incorporated by reference.

EXAMPLE 1

Compound (1) is Prepared According to the Following Reaction Scheme

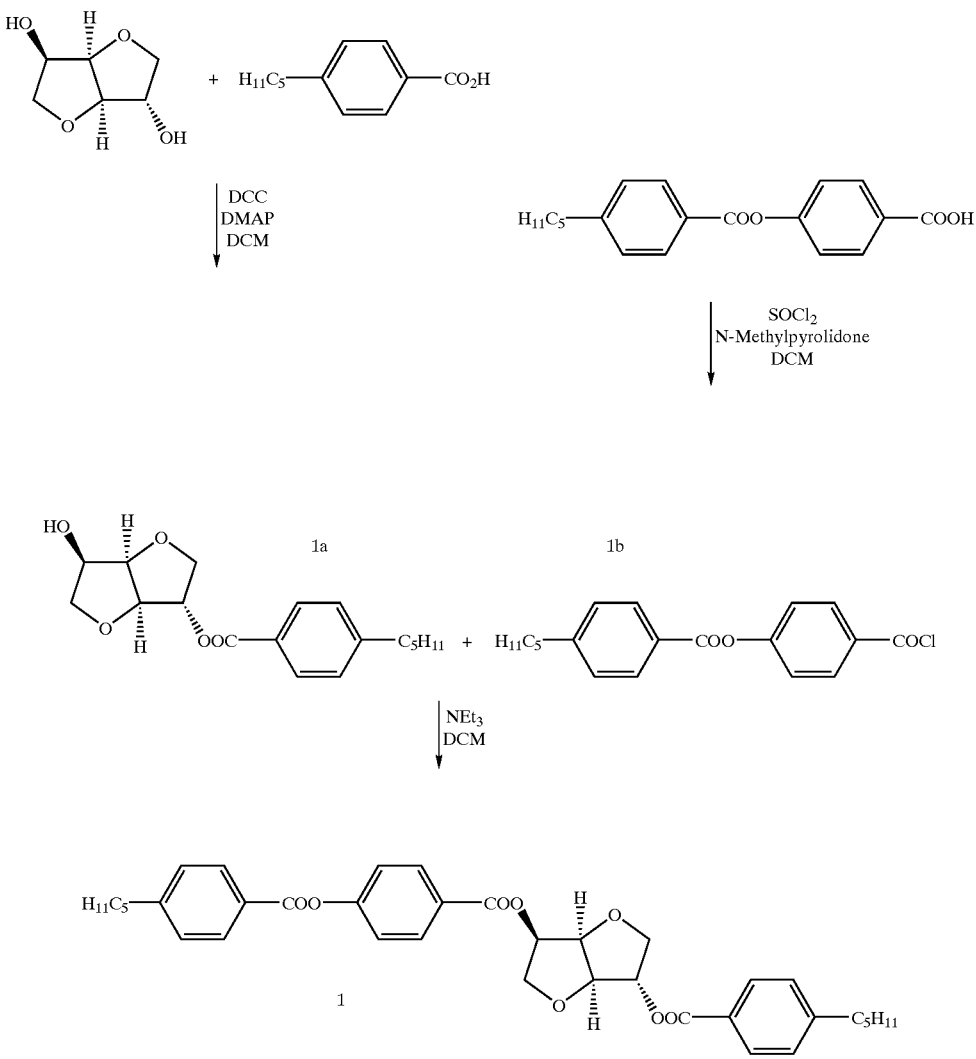

Preparation of Monoester (Compound 1a)

Isosorbide (3.8 g, 0.026 mol), 4-n-pentylbenzoic acid (5.0 g, 0.026 mol) and N,N'-dicyclohexylcarbodiimide (5.36 g, 0.052 mol) were combined in dichloromethane (100 ml). 4-Dimethylaminopyridine (0.1 g, catalyst) was added and the reaction mixture was stirred at room temperature overnight with the exclusion of moisture (CaCl$_2$ guard tube). N,N-Dicyclohexylurea was filtered off and the filtrate was washed with water (3×100 ml), dried with anhydrous Na$_2$SO$_4$ and the solvent removed under reduced pressure using a rotary evaporator. The crude product was flash column chromatographed over MERCK 40–63 μm silica gel, eluting with 3:2 toluene: ethyl acetate; 4.1 μg (49.5%) yield.

Preparation of Acid Chloride (Compound 1b)

The two ring acid (1.55 g, 0.00496 mol) and thionyl chloride (0.64 g, 0.00546 mol) were combined in dichloromethane (20 ml). N-Methylpyrollidone was added and the reaction mixture was stirred and refluxed until a clear solution was obtained and then for a further 2 hours. Reaction mixture was evaporated to dryness under reduced pressure using a rotary evaporator. The crude product was used in the next step without further purification.

Preparation of Unsymmetrical Diester (Compound 1)

Monoester (1.44 g, 0.00451 mol), triethylamine (2.28 g, 0.0025 mol) and dichloromethane (20 ml) were combined with stirring at 25° C. Acid chloride (1.64 g, 0.00496 mol) in dichloromethane (20 ml) was added dropwise and the reaction mixture was stirred for 24 hours in a nitrogen atmosphere. The reaction mixture was then poured into water and extracted with dichloromethane (50 ml). The organic extract was washed with water, dried with anhydrous Na$_2$SO$_4$ and the solvent was removed under reduced pressure using a rotary evaporator. The crude product was flash columned over MERCK 40–63 μm silica gel, eluting with dichloromethane. The columned material was recrystallised from ethanol and dried in a vacuum oven at 40° C. for 24 hours; 0.92 g (33.2%) yield.

The following compounds can be prepared analoguously

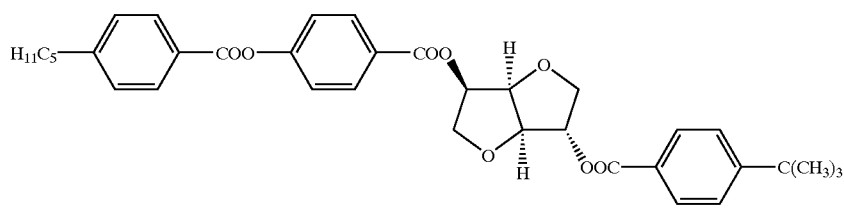

2

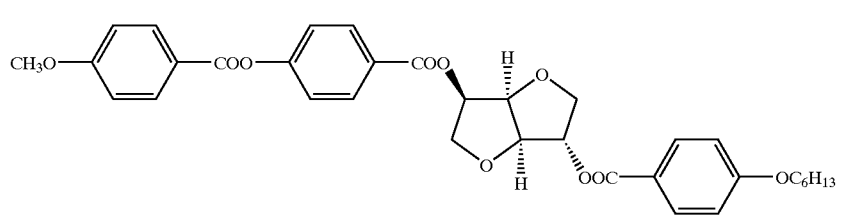

3

The corresponding isomers 1*, 2* and 3* of compounds 1–3, where the two-ring is at the 2-position of the isosorbide core, were prepared analoguously using the two ring acid in the first step.

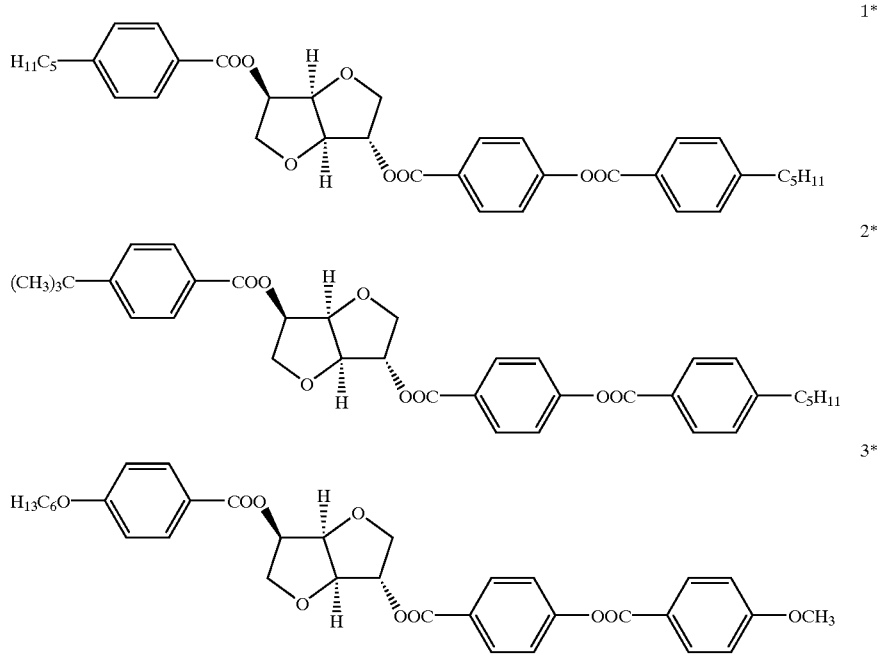

The HTP and temperature dependence of the reflection wavelength in the temperature range from −20° C. to +80° C. of compounds 1–3 and their isomers 1*-3* were measured in the nematic host mixture BL087 at a concentration of 5%. The solubility of compounds 1–3 and their isomers 1*-3* was measured by preparing a mixture of the respective compound in BL087 at a concentration of 20%. The mixtures were allowed to stand at room temperature for 1 week to allow for crystallistion. Then the mixtures were filtered, the reflection wavelength measured and the concentration of the chiral compound remaining in the mixture calculated from the known HTP of the compounds. The results are shown in table 1.

TABLE 1

Comparison of compounds 1–3 and their isomers 1*-3*

| No. | mp. [° C.] | HTP [$\mu m^{-1}$] | $d\lambda/dT$ [nm/° C.] | Solubility at room temp. |
|---|---|---|---|---|
| 1 | 101.6 | 63.7 | 0.18 | 15.3% |
| 1* | 116.4 | 60.4 | 0.16 | 4.2% |

TABLE 1-continued

Comparison of compounds 1–3 and their isomers 1*–3*

| No. | mp. [° C.] | HTP [μm⁻¹] | dλ/dT [nm/° C.] | Solubility at room temp. |
|---|---|---|---|---|
| 2 | 112.8 | 69.8 | 0.73 | 11.8% |
| 2* | 140.4 | 50.8 | 0.46 | 2.3% |
| 3 | 121.8 | 67.4 | 0.09 | 4.1% |
| 3* | 129.8 | 62.1 | 0.32 | 0.8% |

Compounds 1–3 according to the present invention have higher HTP and considerably higher solubility in the nematic host mixture than their isomers 1*–3*.

What is claimed is:

1. A chiral compound of formula I:

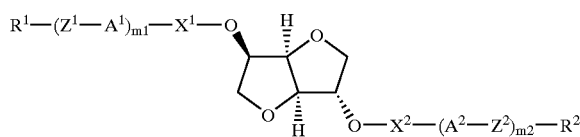

I wherein
R$^1$ and R$^2$ are, independently of each other, P—Sp—X, F, Cl, Br, I, CN, SCN, SF$_5$, or a straight chain or branched alkyl with 1 to 30 C atoms that is unsubstituted, mono- or poly-substituted by F, Cl, Br, I or CN, and wherein one or more non-adjacent CH$_2$ groups are optionally replaced, in each case independently from one another, by —O—, —S—, —NH—, —NR$^0$—, —CO—, —COO—, —OCO—, —OCO—O—, —S—CO—, —CO—S—, —CH=CH— or —C≡C—in a manner that O and/or S atoms are not linked directly to one another,
R$^0$ is H or alkyl with 1 to 4 C atoms,
P is a polymerizable group,
Sp is a spacer group or a single bond,
X is —O—, —S—, —OCH$_2$—, —CH$_2$O—, —CO—, —COO—, —OCO—, —OCO—O—, —CO—NR$^0$—, —NR$^0$—CO—, —OCH$_2$—, —CH$_2$O—, —SCH$_2$—, —CH$_2$S—, —CH=CH—COO—, —OOC—CH=CH— or a single bond,
X$^1$ is —CO—, —OCO—, —NR$^0$—CO—, —CH=CH—CO—, —CH$_2$—, —C$_2$H$_4$—, —CF$_2$— or a single bond,
X$^2$ is —CO—, —COO—, —CO—NR$^0$—, —CO—CH=CH—, —CH$_2$—, —C$_2$H$_4$—, —CF$_2$— or a single bond,
Z$^1$ and Z$^2$ are, independently of each other, —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CH—, —CF=CH—, —CH=CF—, —CF=CF—, —C≡—C—, —CH=CH—COO—, —OCO—CH=CH— or a single bond,
A$^1$ and A$^2$ are, independently of each other, an aliphatic or aromatic carbocyclic or heterocyclic group with 1 to 16 C atoms that optionally contains one or more fused rings and is unsubstituted, mono- or polysubstituted with L,
L is halogen or a cyano, nitro, alkyl, alkoxy, alkylcarbonyl or alkoxycarbonyl group with 1 to 7 C atoms, wherein one or more H atoms are optionally substituted by F or Cl,
m1 is 1, 2 or 3, and
m2 is 0, 1, 2 or 3,
with the proviso that the total number of fused or unfused rings in the (Z$^1$–A$^1$)$_{m1}$ group is larger than in the (A$^2$–Z$^2$)$_{m2}$ group.

2. A chiral compound according to claim 1, wherein A$^1$ and A$^2$ are, independently of each other, 1,4-phenylene wherein one or more CH groups are optionally and independently of each other, replaced by N; 1,4-cyclohexylene wherein one or two non-adjacent CH$_2$ groups are optionally and independently of each other, replaced by O or S; 1,3-dioxolane-4,5-diyl; 1,4-cyclohexenylene; or piperidine-1,4-diyl, wherein any of said groups being unsubstituted, mono- or polysubstituted with L, and wherein m1>m2.

3. A chiral compound according to claim 1, wherein m1 is 2 and m2 is 1.

4. A chiral compound according to claim 1, wherein X$^1$ and X$^2$ are —CO—.

5. A chiral compound according to claim 1, wherein A$^1$ and A$^2$ are, independently of each other, trans-1,4-cyclohexylene or 1,4-phenylene, which is unsubstituted or substituted with 1 to 4 L groups.

6. A chiral compound according to claim 1, wherein Z$^1$ and Z$^2$ are, independently of each other, —COO—, —OCO— or a single bond.

7. A chiral compound according to claim 1, wherein R$^1$ or R$^2$ or both R$^1$ and R$^2$ is a polymerizable P—Sp—X group.

8. A chiral compound according to claim 1, which is of the following formulae:

I-1

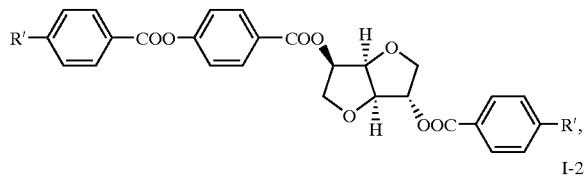

I-2

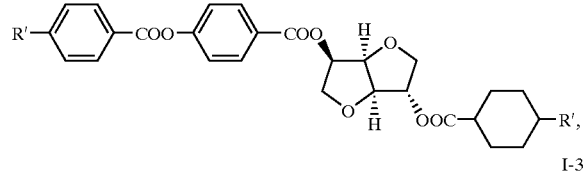

I-3

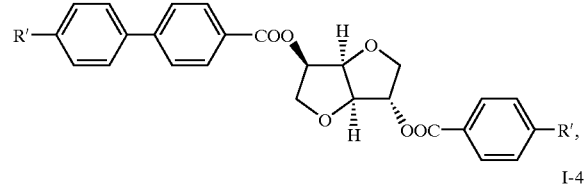

I-4

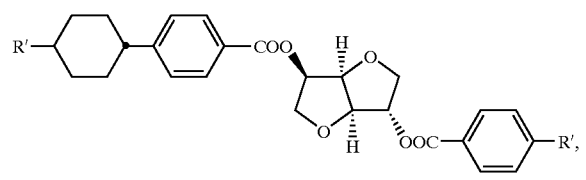

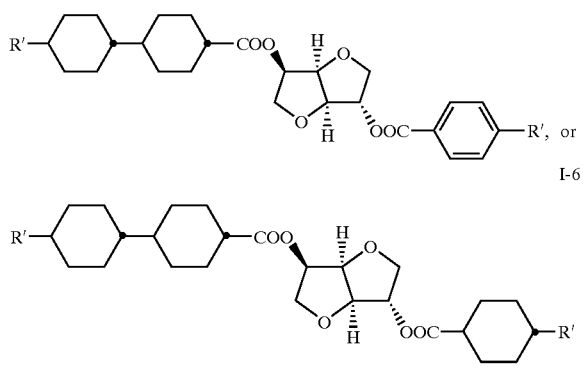

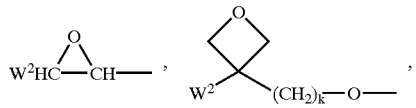

wherein
R¹ and R' are, independently of each other, P—Sp—X, F, Cl, Br, I, CN, SCN, SF₅, or a straight chain or branched alkyl with 1 to 30 C atoms that is unsubstituted, mono- or poly-substituted by F, Cl, Br, I or CN, and wherein one or more non-adjacent CH₂ groups are optionally replaced, in each case independently from one another, by —O—, —S—, —NH—, —NR⁰—, —CO—, —COO—, —OCO—, —OCO—O—, —S—CO—, —CO—S—, —CH=CH— or —C≡C— in a manner that O and/or S atoms are not linked directly to one another, and wherein any phenylene ring is optionally substituted with 1, 2 or 3 L groups.

9. A liquid crystal mixture comprising at least one chiral compound according to claim 1.

10. A polymerizable liquid crystal mixture comprising at least one compound of formula I according to claim 1 and at least one polymerizable mesogenic compound, which is optionally a compound of formula I.

11. A chiral linear or crosslinked liquid crystal polymer obtained by polymerizing a mixture according to claim 10.

12. An STN, TN, AMD-TN, temperature compensation, ferroelectric, guest-host, phase change, surface stabilized or polymer stabilized cholesteric texture display, an active or passive optical element polarizer, a compensator, an alignment layer, color filter, a polymer film, a cholesteric broadband polarizer, a retardation film, a holographic element, an adhesive, a synthetic resin with anisotropic mechanical properties, a cosmetic or pharmaceutical composition, a UV filter, a diagnostics element, a liquid crystal pigment, a decorative and security marking, a nonlinear optics element, an optical information storage element, or a chiral dopant comprising a chiral compound according to claim 1, or a liquid crystal mixture comprising said chiral compound, or a chiral linear or crosslinked liquid crystal polymer obtained by polymerizing said mixture.

13. A liquid crystal display comprising a liquid crystal mixture according to claim 9.

14. A cholesteric liquid crystal mixture comprising at least one chiral compound according to claim 1, and one or more nematic or nematogenic compounds.

15. A cholesteric or SSCT display comprising a mixture according to claim 14.

16. A color filter, a broadband reflective polarizer, a patterned film or a security marking comprising a polymerizable mixture according to claim 10 which has been polymerized.

17. A chiral compound according to claim 1, wherein P is a vinyl group, an acrylate group, a methacrylate group, a propenyl ether group, an epoxy group, $CH_2=CW^1$—$COO$—, $W^2HC$—$CH$—, $W^2$—$(CH_2)_k$—$O$—, $CH_2=CW^2$—$(O)_{k1}$—, $CH_3$—$CH=CH$—$O$—, $HO$—$CW^2W^3$—, $HS$—$CW^2W^3$—, $HW^2N$—, $HO$—$CW^2W^3$—$NH$—, $CH_2=CW^1$—$CO$—$NH$—, $CH_2=CH$—$(COO)_{k1}$—$Phe$-$(O)_{k2}$—, $Phe$-$CH=CH$—, $HOOC$—, $OCN$— or $W^4W^5W^6Si$—, wherein $W^1$ is H, Cl, CN, phenyl or alkyl with 1 to 5 C-atoms, $W^2$ and $W^3$ are, independently of each other, H or alkyl with 1 to 5 C-atoms, $W^4$, $W^5$ and $W^6$ are, independently of each other, Cl, oxaalkyl or oxacarbonylalkyl with 1 to 5 C-atoms, Phe is 1,4-phenylene, and $k_1$ and $k_2$ are, independently of each other, 0 or 1.

18. A chiral compound according to claim 1, wherein Sp is a linear or branched alkylene group having 1 to 20 C atoms, in which one or more non-adjacent CH₂ groups are optionally replaced by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in a manner that O and/or S atoms are not linked directly to one another, wherein R⁰ and R⁰⁰ are, independently of each other, H or alkyl with 1 to 4 C-atoms, or wherein Sp is a chiral group of formula IV:

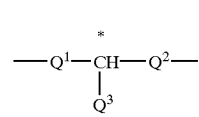

IV wherein
Q¹ is an alkylene or alkylene-oxy group with 1 to 10 C atoms or a single bond,
Q² is an alkylene or alkylene-oxy group with 1 to 10 C atoms or a single bond, which is different from Q¹, and
Q³ is halogen, a cyano group or an alkyl or alkoxy group with 1 to 4 C atoms, which is different from Q².

19. A chiral compound according to claim 1, wherein A¹ and A² are, independently of each other, cyclopentane, 1,1,-dimethylcyclopentane, tetrahydrofuran, pyrrolidine, furan, pyrrol, thiophene, oxazole, thiazole, thiadiazole, imidazole, pyrrolidinone, cyclohexane, cyclohexene, tetrahydropyran, piperidine, tetrahydrothiopyrane, dioxane, dithiane, oxathiane, thiomorpholine, morpholine, phenylene, pyridine, pyrimidine, pyrazine, bicyclohexane, bicyclohexene, cyclohexane-1,4-dione, bicyclo[2,2,2]octylene, cyclohexenone, indane, naphthalene, decahydronaphthalene, 1,2,3,4-tetrahydronaphthalene, anthracene, phenanthrene, 1,4-phenylene in which one or more CH groups are optionally replaced by N, 1,4-cyclohexylene in which one or two non-adjacent CH₂ groups are optionally replaced by O and/or S, 1,3-dioxolane-4,5-diyl, 1,4-cyclohexenylene, 1,4-bicyclo-(2,2,2)-octylene, piperidine-1,4-diyl, naphthalene-2,6-diyl, decahydronaphthalene-2,6-diyl, 1,2,3,4-tetrahydronaphthalene-2,6-diyl, or indane-2,5-diyl, wherein all these groups are unsubstituted, mono- or polysubstituted by L.

20. A chiral compound according to claim 1, wherein $R^1$ or $R^2$ is of formula III:

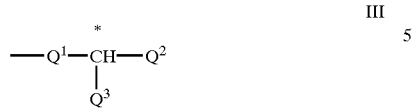

III wherein $Q^1$ is an alkylene or alkylene-oxy group with 1 to 9 C atoms or a single bond, $Q^2$ is an alkyl or alkoxy group with 1 to 10 C atoms which is unsubstituted, mono- or polysubstituted by F, Cl, Br or CN, wherein one or more non-adjacent $CH_2$ groups are optionally replaced, in each case independently from one another, by —C≡C—, —O—, —S—, —NH—, —N(CH₃)—, —CO—, —COO—, —OCO—, —OCO—O—, —S—CO— or —CO—S— in a manner that oxygen atoms are not linked directly to one another, and $Q^3$ is F, Cl, Br, CN or an alkyl or alkoxy group as defined for $Q^2$ but which is different from $Q^2$.

* * * * *